United States Patent [19]

Fearnot et al.

[11] Patent Number: 5,069,674
[45] Date of Patent: Dec. 3, 1991

[54] FLEXIBLE, KINK-RESISTANT CATHETER

[75] Inventors: Neal E. Fearnot; Richard B. Sisken, both of West Lafayette, Ind.

[73] Assignee: Medical Engineering and Development Institute, Inc., West Lafayette, Ind.

[21] Appl. No.: 458,610

[22] Filed: Dec. 29, 1989

Related U.S. Application Data

[63] Continuation-in-part of Ser. No. 275,435, Nov. 23, 1988, Pat. No. 4,985,022.

[51] Int. Cl.⁵ .............................................. 7A61 25/00
[52] U.S. Cl. ...................................... 604/282; 604/280
[58] Field of Search ..................... 604/282, 280, 96; 128/656–658; 138/174, 132, 133, 146

[56] References Cited

U.S. PATENT DOCUMENTS

| | | | |
|---|---|---|---|
| 3,913,565 | 10/1975 | Kawahara | 604/96 |
| 4,052,989 | 10/1977 | Kline | 604/282 |
| 4,368,730 | 1/1983 | Sharrock . | |
| 4,385,635 | 5/1983 | Ruiz . | |
| 4,515,587 | 5/1985 | Schiff | 604/282 |
| 4,580,568 | 4/1986 | Gianturco | 604/96 |
| 4,596,563 | 6/1986 | Pande . | |
| 4,737,153 | 4/1988 | Shimamura | 604/282 |
| 4,784,639 | 11/1988 | Patel . | |
| 4,842,590 | 6/1989 | Tanabe et al. | 604/282 |
| 4,884,573 | 12/1989 | Wijay et al. | 604/282 |
| 4,917,666 | 4/1990 | Solar et al. | 604/96 |
| 4,976,720 | 12/1990 | Machold et al. | 604/95 |
| 4,985,022 | 1/1991 | Fearnot et al. | 604/280 |

Primary Examiner—Stephen C. Pellegrino
Assistant Examiner—Ralph A. Lewis
Attorney, Agent, or Firm—Richard J. Godlewski

[57] ABSTRACT

An extremely small diameter epidural catheter is disclosed which is both flexible and kink-resistant when flexed. The catheter includes a tubular sheath or tube having a passageway therein for the delivery of fluids to biological tissue. Positioned in the passageway is a coil which is expansion-fitted therein to form a composite wall structure which is extremely flexible and kink-resistant. This composite wall structure is utilized to form a catheter having an extremely small outside diameter in a range of 0.010" to 0.032" for delivering acceptable levels of fluid volume. The coil comprises a plurality of closely spaced turns extending from the proximal to almost the distal end thereof. About the distal end of the coil is a number of loosely coupled or relaxed turns which adds further flexibility to the distal end of the catheter. The tubular sheath of the catheter comprises a high tensile or flexural strength material which does not rupture or tear when the catheter is bent or flexed. Maintaining the ratio of the outside diameter of the wire coil to the cross-sectional diameter of the individual turns within a range of 4 to 10 prevents the tubular sheath from either rupturing or kinking when the catheter is flexed or bent.

20 Claims, 1 Drawing Sheet

5,069,674

FLEXIBLE, KINK-RESISTANT CATHETER

CROSS-REFERENCE TO RELATED APPLICATION

This application is a continuation-in-part of application Ser. No. 07/275,435, filed Nov. 23, 1988, now U.S. Pat. No. 4,985,022.

TECHNICAL FIELD

This invention relates to catheters and, in particular, small diameter catheters which are flexible and kink-resistant.

BACKGROUND OF THE INVENTION

Catheters of various types and sizes have been used by physicians extensively. One use of the catheter is in providing regional anesthesia which produces profound analgesia with minimal physiologic alterations. When used at the start of an operation, regional anesthesia minimizes the total dosage of inhalation or intravenous anesthetic drugs required, hastens awakening, and permits early ambulation. When administered at the conclusion of surgery, regional anaesthesia produces post-operative analgesia with reduced risk of respiratory depression. Furthermore, certain types of pain are difficult to treat with systemic narcotics. For example, a bladder spasm following genitourinary surgery may be exacerbated by systemic opioids but is easily treated with a caudal epidural block. When prolonged analgesia is required, a catheter is inserted into the caudal or lumbar epidural space to provide intermittent or continuous injections of local anesthetics.

Caudal epidural anesthesia is notable for its simplicity, safety, and effectiveness and is one of the most frequently used regional anesthetic techniques for operations below the diaphragm in children.

When continuous pain relief is desired, the only equipment presently available is either a 19 or 20 gauge epidural catheter which is passed through either a 17 gauge Tuohy or an 18 gauge Crawford needle. Designed specifically for adults, these needles are approximately 3 ½" long and have an outside diameter ranging from 0.050" to 0.059" along with an inside diameter ranging from 0.033" to 0.041". However, these needles are extraordinarily cumbersome to use in children, since the distance from the skin to the epidural space is only 10-15mm. Obviously, smaller needles and catheters are desirable.

The smallest presently offered epidural catheter is a 20 gauge continuous epidural catheter with an outside diameter of approximately 0.035". This catheter is constructed of a spiral wound stainless steel helix with a polymer plastic coating on the outside surface of the helix. The outside surface of the polymer coating is smooth, whereas the inside surface of the coating conforms to the outer surface of the spiral helix. The spiral helix is tightly wound with adjacent windings being in physical contact with each other. In effect, a spiral groove is formed in the outside surface of the helix in which the polymer coating conforms. As a result, the thickness of the polymer coating varies according to the contour of the outside surface of the helix. A problem with this nonuniform thickness coating occurs when the catheter is flexed or bent subjecting the polymer coating to forces that are more than sufficient to rupture or tear the polymer coating. Since the coating is not allowed to slide or move longitudinally over the outside surface of the helix, the polymer coating easily ruptures or tears when the catheter is flexed or bent. Not only is the polymer coating susceptible to being easily ruptured when flexed, the coating has fluid pressure limitations as well.

Another problem with this catheter is that the windings at the distal end of the spring wire helix are uncoated and have been expanded to permit dispersal of an injectate. A safety ribbon wire attached to the distal end prevents stretching of the helix. However, these uncoated and expanded distal windings are susceptible to the ingrowth of tissue, particularly with long-term placement. With tissue ingrowth, removal of the catheter causes trauma to the insertion site as well as possible injury to the dura.

Even with the failures of others, it is still desirable to reduce the outside diameter of a catheter to as small a value as is practical. Merely reducing the dimensions of existing catheters, however, introduces significant problems, one of them being that one must maintain a minimum fluid volume delivery rate.

Delivering a minimum level of fluid volume at an acceptable flow rate and pressure with a small diameter catheter is limited by the inside diameter of the catheter, the thickness of the catheter wall, and the pressure at which the fluid is delivered to the catheter. Calculating the fluid volume at a prescribed flow rate and pressure for a given inside diameter of a catheter is a straightforward matter. However, simply reducing the outside diameter of the catheter, while maintaining the inside diameter, decreases the thickness of the catheter wall and introduces a number of other concerns. These concerns include the susceptibility of the catheter to kinking when flexed or bent and the maximum pressure at which the fluid may be delivered without rupturing the catheter wall. As the thickness of the catheter wall decreases, susceptibility of the catheter to kinking increases. At a minimum, kinking of the catheter wall reduces the fluid volume delivery rate and, in many cases, causes a fluid stoppage and a rupture of the catheter wall with an accompanying loss of fluid. Furthermore, the reduced wall thickness must be capable of withstanding the delivery pressure without a rupture of the wall.

Flexibility of the catheter is increased with thinner wall thicknesses. However, the susceptibility of the catheter to kinking when flexed or bent also increases along with the probability of rupture due to kinking or high fluid pressures.

Minimum fluid volume delivery rates may be maintained with an increased delivery pressure when the inside and outside diameters of the catheter are decreased. However, an increase in delivery pressure must not cause injury to the tissue in the vicinity of a catheter. Delivery pressure is also limited by the connector attached at the proximal end of the catheter.

A number of small diameter catheters less than 0.033" have been attempted with one or more layers of polymer plastic material. However, the interrelationship between flexibility, kink-resistance, and fluid delivery pressure has prevented the introduction of an all plastic material catheter that is less than 0.033" in diameter and that is flexible, kink-resistant, and capable of delivering a volume of fluid at a rate which is acceptable by the medical community.

SUMMARY OF THE INVENTION

The foregoing problems are solved and a technical advance is achieved in an illustrative flexible and kink-resistant catheter for insertion into biological tissue for withstanding abusive environments external to the patient and for atraumatic insertion and extraction from patient tissue. This catheter advantageously employs a flexible, thin-wall structure comprising a tubular sheath and an elongated coil positioned within the longitudinal passageway of the tubular sheath. The sheath or tube is comprised of a minimum tensile or flexural strength material to minimize rupturing. The coil is either friction-fitted within the sheath or has a circumference that is in contact with the inside surface of the tubular sheath to improve the kink-resistance of the flexible sheath.

This combined catheter wall structure provides a flexible, kink-resistant catheter with an outside diameter in a range of 0.010" to 0.032" while providing acceptable delivery rates of fluid volume. This constitutes a significant departure in the art.

The tubular sheath or tube of the catheter is illustratively comprised of a high tensile and flexural material such as polyimide having a nominal tensile strength of at least 20,000 pounds per square inch. This high tensile strength tubular material advantageously provides for the delivery of fluid at more than acceptable volume levels. Flexibility of the catheter wall is maintained with a combined wall thickness in the range of 0.002" to 0.006", which also allows for extremely small outside diameter catheters such as 0.010". The kink-resistance of the catheter wall is maintained at an extremely high level with a friction-fitted elongated spiral coil positioned within the passageway of the tubular sheath. The spiral coil distributes the radial and longitudinal forces over the high tensile strength tube without rupturing the tube when the catheter is flexed or bent. When flexed or bent, the effected coils move within the passageway of the tube to distribute the forces along the surface of the bent tube. The combination of the high tensile and flexural strength tubular sheath material and the spiral coil positioned within the passageway thereof allows the catheter to be virtually tied in a knot and still provide more than adequate levels of fluid volume delivery without rupturing or kinking the catheter.

The spiral coil includes a member such as stainless steel wire having a diameter in a range of 0.001" to 0.003". As a result, the coil has an outside diameter in a range of 0.008" to 0.026". The flexibility and kink-resistance feature of the catheter are advantageously maintained when the ratio of the member diameter to the outside coil diameter is in a range of 4 to 10. When outside the limits of this range, the tubular sheath when flexed or bent is either ruptured or kinked with the prevention of fluid flow within the passageway thereof.

To further increase the flexibility of the distal end of the catheter, the turns of the spiral coil are relaxed so as to provide a spacing therebetween which is in contrast to the tightly coupled turns throughout the remaining portion of the catheter. A safety wire is extended throughout the length of the passageway and attached about the opposite ends of the coil to provide a further measure of safety. Alternatively, a safety wire is spirally coiled around the external surface of the spiral coil and friction-fitted into the passageway of the tubular sheath.

To reduce, if not eliminate, turbulent fluid flow, a tube is inserted in the passageway of the coil. Furthermore, the need for anticoagulants in a turbulent fluid flow delivery system is all but eliminated.

DETAILED DESCRIPTION

Figure 1:
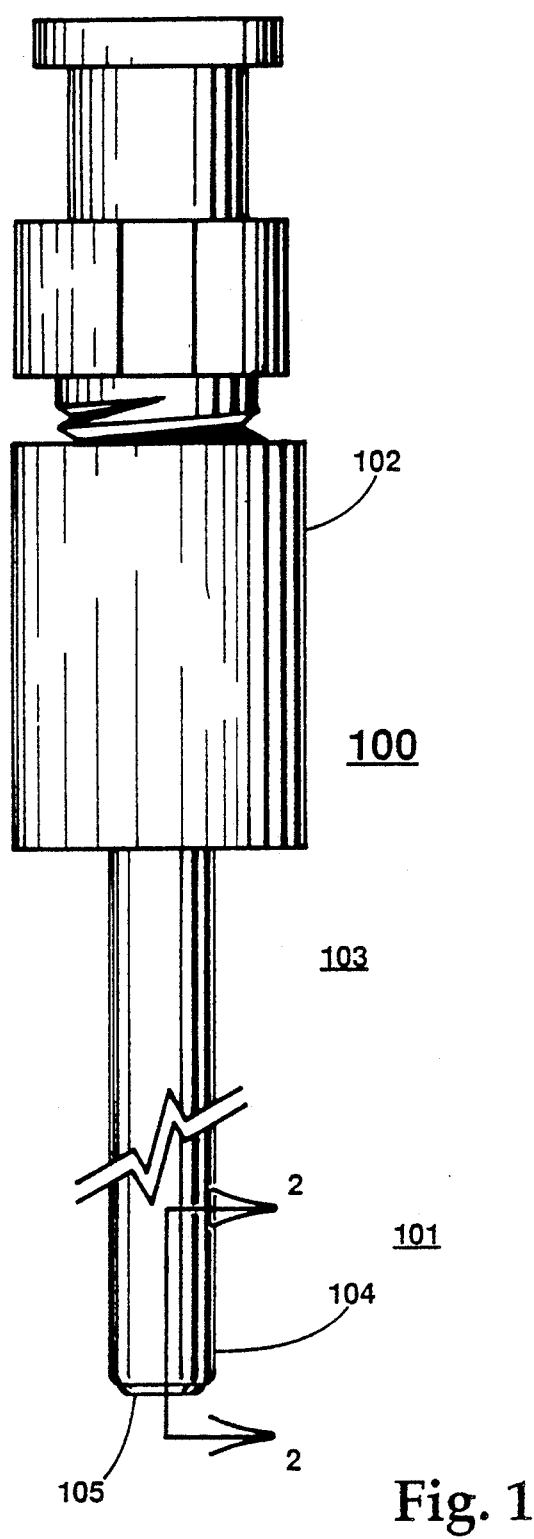
FIG. 1 depicts a flexible, kink-resistant catheter of the present invention.

Depicted in FIG. 1 is an illustrative epidural catheter 100 having a flexible, kink-resistant segment 101 which is passable through an aperture having a diameter less than 0.033". A catheter segment with an outside diameter as small as 0.010" is available for insertion through a Tuohy or Crawford thin-wall needle as small as 25-gauge. After the needle is inserted in the spine, the epidural catheter is inserted through the hollow passageway of the needle into the epidural or caudal space. When the catheter is in place, the needle is removed over the entire length of the catheter, and a well-known and commercially available medical grade connector 102, such as a Tuohy-Borst connector, which is available from Cook, Inc., is attached to the proximal end 103 of the catheter.

The flexible, kink-resistant elongated segment comprises a tubular sheath or tube 104 having a longitudinal passageway in which an elongated wire coil 105 is friction-fitted. The combination of the tubular sheath and the friction-fitted wire coil therein provides the catheter with a thin-wall structure which is both flexible and kink-resistant.

Figure 2:
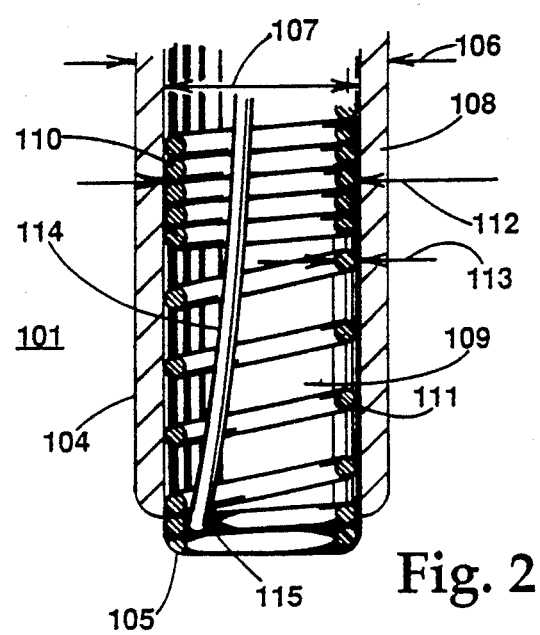
FIG. 2 depicts a partial cross-sectional view of the distal end of the catheter of FIG. 1.

A partial cross-sectional view of flexible elongated segment 101 of the catheter is depicted in FIG. 2. Tubular sheath 104 has an outside diameter 106 in a range of 0.010" to 0.032". The inside diameter 107 of the sheath is in a range of 0.008" to 0.026". The thickness of tubular sheath wall 108 is in range of 0.001" to 0.003". The tubular sheath comprises a material having a high tensile or flexural strength to resist tearing, rupturing, or bursting when either pulled, flexed or bent or when subjected to high pressure fluids therein. The tubular sheath comprises a plastic tube of polyimide material which is available from Micro ML Tubing Sales. This polyimide material tube comprises a flexible, non-flammable, radiation resistant and non-corrosive material. In addition, the polyimide material tubing exhibits a nominal tensile strength of 20,000 pounds per square inch with an even higher flexural strength. This cross-linked polymer allows for a tubular sheath with an extremely small wall thickness for flexibility, but also has an extremely high tensile, as well as flexural, strength to resist rupturing or tearing when flexed or bent. The high tensile and flexural strength also provides for delivering fluids at extremely high pressure levels. Other materials such as polyamide and fluoropolymers having a tensile strength greater than 10,000 pounds per square inch are also acceptable. A variety of commercially-available TEFLON material tubes are also acceptable for low pressure or less kink-resistant applications. Various other copolymer plastic materials may also be acceptable; however, these plastic materials must be capable of being formed into a tubular sheath with the afore-mentioned dimensions. Such extremely small diameter and wall thickness tubing made of these polymer plastic materials have been extremely difficult to extrude or fabricate with these dimensions.

Positioned within longitudinal passageway 109 of tubular sheath 104 is coil 105. Coil 105 comprises an elongated, spirally wound helical wire coil of a hardened stainless steel material. Coil 105 may also be made of other suitable materials such as other metals or alloys, carbon filaments, hard plastic fibers, or combinations thereof.

Coil 105 includes a plurality of closely-coupled turns 110 from the proximal end to almost the distal end of the catheter. Turns 110 of the coil are closely spaced such as to be in physical contact with each other with very little, if any, space between the individual windings or turns. At the distal end of coil 105 is a plurality of loosely coupled turns 111. These loosely coupled turns are formed from the tightly coupled turns by stretching or relaxing the distal end of the coil. The spacing between the turns of 111 provides further flexibility to the distal end of the catheter for atraumatic insertion into biological tissue.

The outside diameter of coil 105 is in a range of 0.008" to 0.026". The cross-sectional diameter of the individual spiral members or turns of coil 105 are within a range of 0.001" to 0.003". Coil 105 is positioned within passageway 109 of the sheath in one of several different ways. By way of a first example, the opposite ends of the coil are turned in opposing directions to cause the outside diameter of the coil to shrink. When the outside diameter of the coil is reduced, the tubular sheath is positioned thereover. The opposite ends of the coil are then released to permit the outside diameter of the turns to expand and form an expansion or friction fit against the inside surface of the tube. This fabrication method is preferred; however, all that is required is that the circumference of the spiral member is in contact with the inside surface of the tubular sheath. This close friction-fit contact between the tubular sheath and wire coil forms the thin-wall structure of the catheter which is extremely flexible and is resistant to rupture or tearing when subjected to bending or flexing.

Experimental results have indicated that when the ratio of the outside coil diameter to the spiral member diameter is maintained in a range of 4 to 10 with a tubular sheath thickness of 0.001" to 0.003", the combined catheter wall structure with a polyimide sheath material does not rupture or kink. When the ratio is below 4, even the high tensile strength polyimide material ruptures or tears. When the ratio exceeds 10, the polyimide material tubular sheath kinks with occlusion of the passageway of the sheath.

Coil 105 such as a hardened stainless steel wire coil with the above cross-sectional dimensions and outside diameters are available from Cook, Inc., as well as other suppliers.

A safety wire 114 extends throughout the entire length of the passageway of the coil and tubular sheath. As shown, the distal ends of the safety wire and coil are attached using silver solder 115. The windings are also shaped in a well-known manner to provide a rounded surface for atraumatic insertion into tissue. The distal end of the tubular sheath may also be rounded for further ease of insertion. The proximal ends of the safety wire and wire coil are also similarly attached. The safety wire prevents the stretching of the wire coil for whatever reason.

Figure 3:
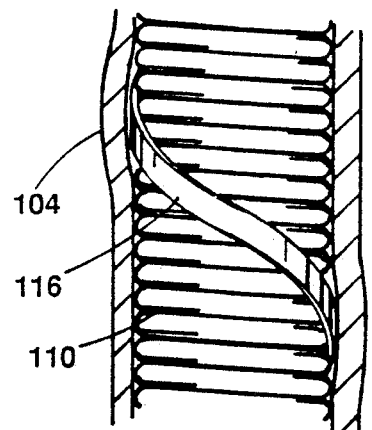
FIG. 3 depicts a second embodiment of the catheter of FIG. 2 with an alternative safety wire.

Depicted in FIG. 3 is an alternative embodiment of a safety wire 116 spirally wound around the outside of the coil and the inside of the tubular sheath.

Figure 4:
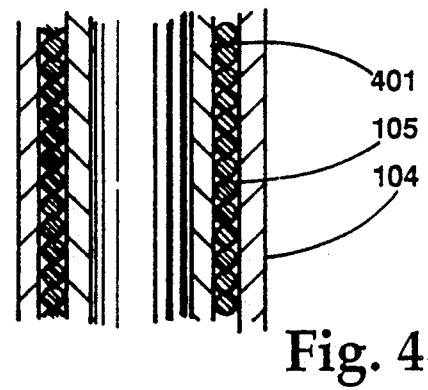
FIG. 4 depicts an alternative embodiment of the catheter of FIG. 1 with a tubular sheath positioned within the passageway of the wire coil.

Depicted in FIG. 4 is a partial cross-sectional view of flexible segment 101 with an inner tube 401 positioned within the passageway of coil 105. As a result, the wall thickness of outside tubular sheath 104 may be reduced. This alternative embodiment provides for a very smooth surface for which fluids without an anticoagulant may be delivered to biological tissue. This is particularly advantageous in those cases of long term insertion of a catheter. In addition, the flow of fluid is laminar rather than turbulent which provides for greater fluid volume delivery rates. Furthermore, the likelihood of particulates in any fluid coagulating around the windings of coil 105 are eliminated.

It is to be understood that the above-described flexible, kink-resistant catheter is merely an illustrative embodiment describing the principles of this invention and that other catheters may be devised by those skilled in the art without departing from the spirit and scope of this invention. In particular, the tubular sheath may be formed of other materials not specifically mentioned herein, but have a minimal tensile or flexural strength for providing the combined wall structure. In addition, the spiral member of the wire coil may be formed from other materials not specifically mentioned herein. The sheath and coil materials may also be preshaped to improve access to any one of a number of curved body passageways. One or both ends of the catheter may be curved, tapered, or shaped to form totally implantable devices such as stents and the like. Slits or ports in the sheath may also be formed to provide side delivery and even greater dispersion of the fluids injected from the distal end of the catheter as described in the parent application. The passageway may further be utilized to insert other medical instruments such as a stylet, another catheter, or a wire guide.

WHAT IS CLAIMED IS:

1. A catheter for insertion into biological tissue, comprising:
    a tubular sheath having a longitudinal passageway therein capable of transporting a fluid to said tissue and a minimum predetermined strength capable of maintaining a predetermined flow rate of said fluid within said passageway when said sheath is flexed; and
    an elongated coil having a first plurality of closely-coupled turns and expansion friction-fitted and longitudinally movable within said longitudinal passageway of said tubular sheath, said coil distributing radial and longitudinal forces over said sheath without rupturing said sheath when said sheath is flexed.

2. The catheter of claim 1 wherein said minimum predetermined strength comprises a nominal tensile strength greater than 3,000 pounds per square inch.

3. The catheter of claim 1 wherein said minimum predetermined strength comprises a tensile strength of at least 20,000 pounds per square inch.

4. The catheter of claim 1 wherein said tubular sheath has an outside diameter less than 0.033".

5. The catheter of claim 4 wherein said tubular sheath and said friction-fitted coil have a combined wall thickness in a range of 0.002" to 0.006".

6. The catheter of claim 1 wherein said tubular sheath comprises a plastic material.

7. the catheter of claim 6 wherein said plastic material comprises polyimide.

8. The catheter of claim 1 wherein said catheter has an outside diameter in a range of 0.010" to 0.032" and said coil includes a spiral member having a cross-sectional member diameter in a range of 0.001" to 0.003".

9. The catheter of claim 8 wherein said spiral member comprises a stainless steel wire.

10. The catheter of claim 8 wherein said tubular sheath has an inside diameter in a range of 0.008" to 0.026".

11. The catheter of claim 1 wherein said coil has a passageway therein and wherein said catheter further comprises a tube positioned within said passageway of said coil.

12. The catheter of claim 1 further comprising a spiral strand positioned around a length of said elongated coil and attached about the opposite ends thereof.

13. The catheter of claim 1 further comprising a strand positioned through a passageway of said coil and attached about the opposite ends thereof.

14. The catheter of claim 1 wherein said coil includes a first plurality of turns and a second plurality of turns extending distally from and more losely coupled than said first plurality of turns.

15. A flexible, kink-resistant catheter for insertion into biological tissue, comprising:
   a tube including a material of a minimum predetermined strength and having a longitudinal passageway therein capable of transporting a fluid to said tissue said tube having an outside diameter less than said 0.33" and a wall thickness in a range of 0.001" to 0.003"; and
   a spiral coil expansion friction-fitted and longitudinally movable within said passageway and having a circumference in contact with an inside surface of said tube, said coil distributing radial and longitudinal forces over said sheath without rupturing said sheath when said sheath is flexed.

16. The catheter of claim 15 wherein said coil includes a member having a cross-sectional member diameter in a range of 0.001" to 0.003".

17. The catheter of claim 16 wherein said coil has an outside diameter in a range of 0.008" to 0.026".

18. The catheter of claim 17 wherein a ratio of said outside coil diameter to said member dimension is in a range of 4 to 10.

19. The catheter of claim 15 further comprising a second tube having a wall thickness in a range of 0.001" to 0.003" and positioned within a longitudinal passageway of said spiral coil.

20. An epidural catheter for insertion into biological tissue, comprising:
   a tubular sheath having a longitudinal passageway therein capable of transporting a fluid to said tissue and comprising a polyimide material having a nominal flexural strength of at least 20,000 pounds per square inch, said sheath having an outside diameter in a range of 0.010" to 0.032" and a wall thickness in a range of 0.001" to 0.003"; and
   a spiral coil of stainless steel wire friction-fitted within said longitudinal passageway of said sheath, said coil having an outside diameter in a range of 0.001" to 0.026", said wire having a diameter in a range of 0.001" to 0.003", said sheath and said coil forming a wall structure having a thickness in a range of 0.002" to 0.006", said outside diameter of said coil to said diameter of said wire forming a ratio in a range of 4 to 10, said coil having a first plurality of turns and a second plurality of turns about the distal end thereof and more loosely coupled than said first plurality of turns.

* * * * *